United States Patent
Singer

(10) Patent No.: US 9,155,728 B2
(45) Date of Patent: Oct. 13, 2015

(54) METHODS AND MATERIALS FOR TREATING ORTHOSTATIC HYPOTENSION OR POSTURAL TACHYCARDIA SYNDROME

(75) Inventor: Wolfgang Singer, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 754 days.

(21) Appl. No.: 12/875,220

(22) Filed: Sep. 3, 2010

(65) Prior Publication Data

US 2011/0053989 A1    Mar. 3, 2011

Related U.S. Application Data

(60) Provisional application No. 61/239,678, filed on Sep. 3, 2009.

(51) Int. Cl.
*A61K 31/44* (2006.01)

(52) U.S. Cl.
CPC ...................................... *A61K 31/44* (2013.01)

(58) Field of Classification Search
None
See application file for complete search history.

(56) References Cited

PUBLICATIONS

Raj et al., Acetylcholinesterase inhibition decreases orthostatic tachycardia in the postural tachycardia syndrome, Circulation, 2004, vol. 110, No. 17, Supplement S, pp. 460. Abstract Only.*

Buyukuysal et al., 3,4-Diaminopyridine and choline increase in vivo acetylcholine release in rat striatum, 1995, European Journal of Pharmacology, vol. 281, pp. 179-185.*
Definition of Acetylcholinesterase from freedictionary.com, accessed from http://www.thefreedictionary.com/acetylcholinesterase on Aug. 28, 2013.*
Lundh et al., Improvement in Neuromuscular Transmission in Myasthenia Gravis by 3,4-Diaminopyridine, 1985, Eur. Arch. Psychiatr. Neurol. Sci., 234, pp. 374-377.*
Sanders, 3,4-Diaminopyridine (DAP) in the treatment of Lambert-Eaton Myasthenic Syndrome (LEMS), 1998, Annals New York Academy of Sciences, vol. 841, pp. 811-816.*
Sanders et al., "A randomized trial of 3,4-diaminopyridine in Lambert-Eaton myasthenic syndrome," *Neurology*, 2000, 54:603-607.
Tim et al., "Lambert-Eaton myasthenic syndrome: Electrodiagnostic findings and response to treatment," *Neurology*, 2000, 54:2176-2178.
Singer, "Acetylcholinesterase inhibition: a novel approach in the treatment of neurogenic orthostatic hypotension," *JNNP*, 2003, 74:1294-1298.

* cited by examiner

*Primary Examiner* — James D Anderson
*Assistant Examiner* — Meghan Finn
(74) *Attorney, Agent, or Firm* — Fish & Richardson P.C.

(57) ABSTRACT

This document provides methods and materials related to treating orthostatic hypotension and/or postural tachycardia syndrome. For example, methods and materials for using a composition containing 3,4-diaminopyridine, 4-aminopyridine, or both to treat patients with orthostatic hypotension, postural tachycardia syndrome, or both orthostatic hypotension and postural tachycardia syndrome are provided.

4 Claims, 1 Drawing Sheet

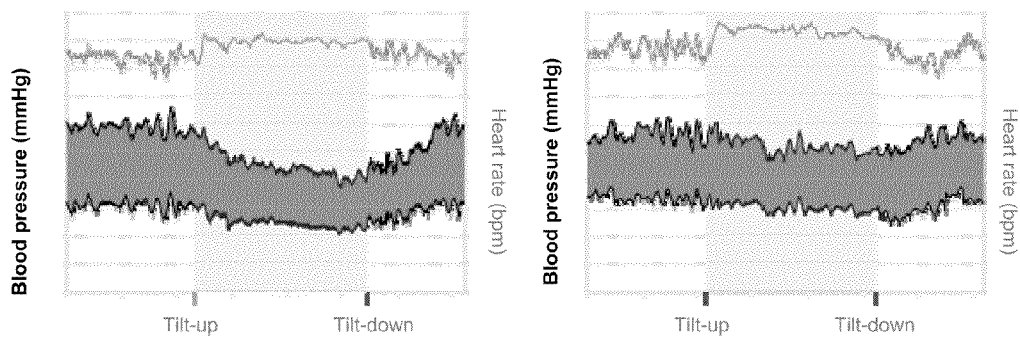

METHODS AND MATERIALS FOR TREATING ORTHOSTATIC HYPOTENSION OR POSTURAL TACHYCARDIA SYNDROME

CROSS-REFERENCE TO RELATED APPLICATIONS

This application claims the benefit of priority to U.S. Provisional Application Ser. No. 61/239,678, filed Sep. 3, 2009. The disclosure of the prior application is considered part of (and is incorporated by reference in) the disclosure of this application.

BACKGROUND

1. Technical Field

This document relates to methods and materials involved in treating orthostatic hypotension or postural tachycardia syndrome. For example, this document relates to methods and materials involved in using a composition containing 3,4-diaminopyridine, 4-aminopyridine, or both to treat patients with orthostatic hypotension, postural tachycardia syndrome, or both orthostatic hypotension and postural tachycardia syndrome.

2. Background Information

Orthostatic hypotension is a disabling condition characterized by inability to maintain adequate blood pressure (BP) in the upright position resulting in lightheadedness and syncope. It occurs frequently in central (multiple system atrophy) and peripheral (autonomic neuropathies, pure autonomic failure) autonomic disorders and is associated with troublesome supine hypertension. The postural tachycardia syndrome (POTS) is also a heterogenous condition characterized by symptomatic excessive orthostatic tachycardia. Treatment options for both disorders are limited and often associated with intolerable side effects including aggravation of supine hypertension.

SUMMARY

This document provides methods and materials related to treating orthostatic hypotension and/or POTS. For example, this document relates to methods and materials involved in using a composition containing 3,4-diaminopyridine (3,4-DAP), 4-aminopyridine, or both to treat patients with orthostatic hypotension, POTS, or both orthostatic hypotension and POTS. In some cases, a composition containing 3,4-DAP, 4-aminopyridine, or both can be administered to reduce the severity or frequency of orthostatic hypotension symptoms and/or POTS symptoms. For example, as described herein, administration of a composition containing 3,4-DAP to a human patient suffering from orthostatic hypotension can essentially prevent the significant orthostatic blood pressure drop that that patient typically experiences following a head-up tilt. In some cases, the methods and materials provided herein can allow clinicians to treat orthostatic hypotension and/or POTS in a human without aggravating supine hypertension, thereby providing the human with a healthier quality of life.

In general, one aspect of this document features a method for treating orthostatic hypotension or postural tachycardia syndrome. The method comprises, or consists essentially of, administering a composition comprising, or consists essentially of, 3,4-diaminopyridine, 4-aminopyridine, or both to a human having orthostatic hypotension or postural tachycardia syndrome under conditions wherein the severity of a symptom of the orthostatic hypotension or the postural tachycardia syndrome is reduced. The method can comprise administering the composition to a human having orthostatic hypotension. The method can comprise administering the composition to a human having postural tachycardia syndrome. The composition can comprise pyridostigmine. The composition can comprise L-threo-dihydroxyphenylserine. The composition can comprise pyridostigmine and L-threo-dihydroxyphenylserine. The composition can comprise midodrine. The method can comprise identifying the human as having the orthostatic hypotension or postural tachycardia syndrome before the administering step. The method can comprise identifying the human as having the orthostatic hypotension before the administering step, and wherein the administering step is under conditions wherein the severity of a symptom of the orthostatic hypotension is reduced. The method can comprise identifying the human as having the postural tachycardia syndrome before the administering step, and wherein the administering step is under conditions wherein the severity of a symptom of the postural tachycardia syndrome is reduced. The method can comprise monitoring the human for the reduction in the severity of the symptom after the administering step.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF THE DRAWINGS

FIG. 1 is a graph plotting the blood pressure and heart rate response to head-up tilt in a patient with orthostatic hypotension before (left) and after (right) oral administration of 20 mg of 3,4-DAP.

DETAILED DESCRIPTION

This document provides methods and materials related to treating a human having orthostatic hypotension and/or POTS. For example, this document relates to methods and materials involved in using a composition containing 3,4-DAP, 4-aminopyridine, or both to treat patients with orthostatic hypotension, POTS, or both orthostatic hypotension and POTS.

In general, orthostatic hypotension and POTS can be treated by administering a composition containing 3,4-DAP, 4-aminopyridine, or both to a human having orthostatic hypotension and/or POTS. Any appropriate method can be used to obtain 3,4-DAP or 4-aminopyridine. For example, 3,4-DAP or 4-aminopyridine can be chemically synthesized or can be obtained commercially from, for example, Jacobus Pharmaceutical Co., Inc. (Princeton, N.J.).

In some cases, a composition containing 3,4-DAP can include 3,4-DAP as the sole active ingredient. In some cases, a composition containing 4-aminopyridine can include 4-aminopyridine as the sole active ingredient. In some cases, a composition containing 3,4-DAP and 4-aminopyridine can include 3,4-DAP and 4-aminopyridine as the sole active ingredients. For example, a composition containing 3,4-DAP or 4-aminopyridine can be formulated to include other ingredients that are not active including, without limitation, fillers, binders, pharmaceutically acceptable vehicles, methyl cellulose, ethanol, various oils such as peanut oil, and dimethyl sulfoxide. A pharmaceutically acceptable vehicle can be, for example, saline, water, lactic acid, and mannitol. In some cases, a composition containing 3,4-DAP, 4-aminopyridine, or both can include additional active ingredients such as pyridostigmine, L-threo-dihydroxyphenylserine (L-DOPS), or midodrine. For example, a composition provided herein can include 3,4-DAP and pyridostigmine or can include 3,4-DAP, pyridostigmine, and L-DOPS.

A composition containing 3,4-DAP, 4-aminopyridine, or both can be in any appropriate form. For example, a composition provided herein can be in the form of a tablet, pill, capsule, solution, or powder.

Any appropriate method can be used to administer a composition containing 3,4-DAP, 4-aminopyridine, or both to a human. For example, a composition containing 3,4-DAP, 4-aminopyridine, or both can be administered orally or via injection (e.g., subcutaneous injection, intramuscular injection, intravenous injection, or intrathecal injection). In some cases, a composition containing 3,4-DAP, 4-aminopyridine, or both can be administered by different routes. For example, one composition containing 3,4-DAP can be administered orally and a second composition containing 3,4-DAP can be administered via injection.

Before administering a composition containing 3,4-DAP, 4-aminopyridine, or both to a human, the human can be assessed to determine whether or not the human has orthostatic hypotension and/or POTS. Any appropriate method can be used to determine whether or not a human has orthostatic hypotension and/or POTS. For example, a mammal (e.g., human) can be identified as having orthostatic hypotension or POTS using standard diagnostic techniques such as measuring blood pressure and heart rate during tilt-table testing or active standing.

After identifying a human as having orthostatic hypotension and/or POTS, the human can be administered a composition containing 3,4-DAP, 4-aminopyridine, or both. A composition containing 3,4-DAP, 4-aminopyridine, or both can be administered to a human in any amount, at any frequency, and for any duration effective to achieve a desired outcome (e.g., to reduce a symptom of orthostatic hypotension and/or POTS). In some cases, a composition containing 3,4-DAP, 4-aminopyridine, or both can be administered to a human having orthostatic hypotension and/or POTS to reduce a symptom of orthostatic hypotension and/or POTS 5, 10, 25, 50, 75, 80, 85, 90, 95, or 100 percent. Any method can be used to determine whether or not the severity of a symptom of orthostatic hypotension and/or POTS is reduced. For example, the severity of a symptom of orthostatic hypotension and/or POTS can be assessed by determining improvement of symptoms upon standing or repeating a tilt-table test.

An effective amount of a composition containing 3,4-DAP, 4-aminopyridine, or both can be any amount that reduces the severity of a symptom of orthostatic hypotension and/or POTS without producing significant toxicity to the human. For example, an effective amount of a composition containing 3,4-DAP can be that amount that contains from about 0.05 mg of 3,4-DAP/kg of body weight to about 10 mg/kg (e.g., from about 0.05 mg/kg to about 5 mg/kg, from about 0.05 mg/kg to about 1 mg/kg, from about 0.1 mg/kg to about 1 mg/kg, or from about 0.1 mg/kg to about 0.5 mg/kg). Typically, an effective amount of a composition containing 3,4-DAP can contain from about 5 mg to about 50 mg of 3,4-DAP. For example, an effective amount of a composition containing 4-aminopyridine can be that amount that contains from about 0.05 mg of 4-aminopyridine/kg of body weight to about 10 mg/kg (e.g., from about 0.05 mg/kg to about 5 mg/kg, from about 0.05 mg/kg to about 1 mg/kg, from about 0.1 mg/kg to about 1 mg/kg, or from about 0.1 mg/kg to about 0.5 mg/kg). Typically, an effective amount of a composition containing 4-aminopyridine can contain from about 5 mg to about 50 mg of 4-aminopyridine.

If a particular human fails to respond to a particular amount, then the amount of 3,4-DAP or 4-aminopyridine can be increased by, for example, two fold. After receiving this higher concentration, the human can be monitored for both responsiveness to the treatment and toxicity symptoms, and adjustments made accordingly. The effective amount can remain constant or can be adjusted as a sliding scale or variable dose depending on the human's response to treatment. Various factors can influence the actual effective amount used for a particular application. For example, the frequency of administration, duration of treatment, use of multiple treatment agents, route of administration, and severity of the orthostatic hypotension and/or POTS may require an increase or decrease in the actual effective amount administered.

The frequency of administration can be any frequency that reduces the severity of a symptom of orthostatic hypotension and/or POTS without producing significant toxicity to the human. For example, the frequency of administration can be from about once a week to about four times a day, or from about twice a month to about six times a day, or from about twice a week to about once a day. The frequency of administration can remain constant or can be variable during the duration of treatment. A course of treatment with a composition containing 3,4-DAP, 4-aminopyridine, or both can include rest periods. For example, a composition containing 3,4-DAP, 4-aminopyridine, or both can be administered daily over a two week period followed by a two week rest period, and such a regimen can be repeated multiple times. As with the effective amount, various factors can influence the actual frequency of administration used for a particular application. For example, the effective amount, duration of treatment, use of multiple treatment agents, route of administration, and severity of the orthostatic hypotension and/or POTS may require an increase or decrease in administration frequency.

An effective duration for administering a composition containing 3,4-DAP, 4-aminopyridine, or both can be any duration that reduces the severity of a symptom of orthostatic hypotension and/or POTS without producing significant toxicity to the human. Thus, the effective duration can vary from several days to several weeks, months, or years. In general, the effective duration for the treatment of orthostatic hypotension and/or POTS can range in duration from several weeks to several months. In some cases, an effective duration can be for as long as an individual human is alive. Multiple factors can influence the actual effective duration used for a particular treatment. For example, an effective duration can vary with the frequency of administration, effective amount, use of multiple treatment agents, route of administration, and severity of the orthostatic hypotension and/or POTS.

After administering a composition provided herein to a human, the human can be monitored to determine whether or not the orthostatic hypotension and/or POTS was treated. For example, a human can be assessed after treatment to determine whether or not the severity of a symptom of the orthostatic hypotension and/or POTS was reduced.

The invention will be further described in the following examples, which do not limit the scope of the invention described in the claims.

EXAMPLES

Example 1

Treating Orthostatic Hypotension with 3,4-DAP

The effects of administering 3,4-DAP to a patient with orthostatic hypotension were studied. Briefly, the blood pressure and heart rate response to head-up tilt was studied in a patient with Lambert-Eaton myasthenic syndrome who also suffered from orthostatic hypotension before and after oral administration of 20 mg 3,4-DAP. Before administration of 3,4-DAP, a significant orthostatic blood pressure drop was observed after a head-up tilt (FIG. 1, left). After administration of 3,4-DAP, the patient did not exhibit a significant orthostatic blood pressure drop after a head-up tilt (FIG. 1, right). These results demonstrate that 3,4-DAP can be used to treat orthostatic hypotension.

Example 2

Clinical Trial to Confirm the Use of 3,4-DAP to Treat Orthostatic Hypotension and POTS One objective is to confirm prospectively the efficacy of a single oral 20 mg dose of 3,4-DAP in the treatment of orthostatic hypotension and POTS. This dose is the standard single dose for adults treated with this medication for Lambert-Eaton myasthenic syndrome. Patients are recruited. All patients are to have neurogenic orthostatic hypotension or POTS, defined using the following criteria. Inclusion Criteria for orthostatic hypotension: (1) males or females age 18-75 years; (2) orthostatic blood pressure drop ≥30 mmHg systolic or ≥15 mmHg diastolic within three minutes of head-up tilt; and (3) orthostatic symptoms including weakness, lightheadedness, blurred vision, faintness, and difficulty with concentration and thinking, rated at least at 2 in severity on a numeric scale from 0 to 10. Inclusion criteria for POTS: (1) males or females age 18-55 years; (2) orthostatic heart rate increment ≥30 bpm within 5 minutes of head-up tilt without the presence of orthostatic hypotension; and (3) symptoms of orthostatic intolerance, rated at least at 2 in severity on a numeric scale from 0 to 10. Exclusion criteria for orthostatic hypotension and POTS: (1) pregnant/lactating females—a pregnancy test is required for women of childbearing potential; (2) the presence of failure of other organ systems or systemic illness that can affect autonomic function; (3) concomitant therapy with anticholinergic, alpha- and beta-adrenergic antagonists or other medication which could interfere with testing of autonomic function; and (4) conditions that increase the potential risk of seizures or cardiac arrhythmias.

Study Design/Schedule

The study is a prospective study on the efficacy and tolerability of 3,4-DAP in patients with orthostatic hypotension and POTS. A total of 20 patients with orthostatic hypotension and 20 patients with POTS are enrolled. All patients undergo tests as described in Table 1. Blood pressure, heart rate, and respiration are continuously monitored on a beat-to-beat basis at supine rest and during 70 degree head-up tilt. These recordings are performed before and one hour after administration of the study drug. The duration of each tilt is 5 minutes for patients with orthostatic hypotension and 10 minutes for patients with POTS. A 5 mL blood sample is drawn before and during each tilt (pre- and 1 hour post-treatment) for plasma norepinephrine, epinephrine, and dopamine. The standing sample is drawn at the end of each tilt, after the patient has been standing for 5 minutes or 10 minutes respectively. Following each tilt, all subjects are asked to grade their orthostatic symptoms on a numeric scale from 0 to 10. Prior to medication administration, a pregnancy test is performed in women of childbearing potential, and an EKG and EEG are performed in all subjects. Evidence of prolonged QT-syndrome or of potentially epileptiform potentials results in exclusion from the study. Patients are monitored for potential side effects for at least 2 hours following medication intake. The total study duration is approximately 8 hours.

TABLE 1

| Study schedule |
| --- |
| 1) Admission |
| 2) Written informed consent |
| 3) IV-line insertion |
| 4) Neurological evaluation and GME |
| 5) Pregnancy test |
| 6) EKG and EEG |
| 7) BP and HR recordings (supine and head-up tilt) |
| 8) Plasma catecholamines (supine and head-up tilt) |
| 9) Symptom score |
| 10) Administration of study medication - 1 hour wait |
| 11) BP and HR recordings (supine and head-up tilt) |
| 12) Plasma catecholamines (supine and head-up tilt) |
| 13) Symptom score |
| 14) Questionnaire |
| 15) Documentation of potential side effects |
| 16) Dismissal |

Data Analysis and Statistics

A database is created for this study containing pertinent patient data. Cardiovascular raw data is collected using Labview software which allows for data sampling at a 250 Hz sampling rate, and is stored for off-line analysis. Peak-detection analysis using dedicated software allows for beat-to-beat calculation of systolic, mean, and diastolic blood pressure and beat-to-beat calculations of heart rate. 20 second averages of these data are calculated for each minute of the recording, which minimizes influence from random fluctuations of blood pressure and heart rate. The data analyst is blinded for the treatment status. Statistics are supervised statistician.

For both patient categories (orthostatic hypotension and POTS), assuming a sample size of 20 patients, with a paired t test, two-sided at an alpha level of 0.05, there is an 80% power to detect an effect size of 0.67 (assuming difference in means of 7.700 with a standard deviation of differences of 15.4). The primary analysis comparing (1) orthostatic blood pressure (orthostatic hypotension)/orthostatic heart rate (POTS) and (2) orthostatic symptoms before and after medication is performed using paired t-tests. Similarly, comparisons of secondary variables are done using paired t-tests. Although the sample size is small for multiple regression analyses, such analyses is carried out to explore the extent to which treatment effects is confounded by other factors, including age, etiology, and severity of disease.

Potential Risks and Protection

There is a theoretical risk of cardiac arrhythmias in patients with prolonged QT-syndrome, and of a seizure in patients with epilepsy. Among 132 patients enrolled in studies on 3,4-DAP in myasthenic syndromes, two patients experienced a self-limited seizure after being on the medication for years; a clear cause-effect relationship was not established. There were no noted complications related to cardiac arrhythmias.

In the above described study, every patient is carefully screened by history, EKG, and EEG, and excluded if there is evidence of increased risk. Other possible side effects are mild and include paresthesias, palpitations, loose stools, abdominal discomfort, and increased salivation. All participants are monitored for at least 2 hours after medication intake by highly trained nursing and MD staff. Other risks include those of an IV line insertion and blood draw. Head-up tilt can result in low BP, but syncope can almost always be prevented by tilting the patient back at signs of pending syncope.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for treating orthostatic hypotension or postural tachycardia syndrome in a patient consisting of administering to the patient a composition comprising 3,4-diaminopyridine as the sole active ingredient or 4-aminopyridine as the sole active ingredient of said composition, wherein said 3,4-diaminopyridine or said 4-aminopyridine is effective to reduce the severity of a symptom of said orthostatic hypotension or said postural tachycardia syndrome.

2. The method of claim 1, wherein the patient has postural tachycardia syndrome.

3. The method of claim 1, wherein said composition comprises 3,4-diaminopyridine.

4. The method of claim 1, wherein said composition comprises 4-aminopyridine.

* * * * *